United States Patent [19]

Goldenberg

[11] 4,444,744
[45] Apr. 24, 1984

[54] TUMOR LOCALIZATION AND THERAPY WITH LABELED ANTIBODIES TO CELL SURFACE ANTIGENS

[76] Inventor: Milton D. Goldenberg, 636 Lakeshore Dr., Lexington, Ky. 40502

[21] Appl. No.: 414,729

[22] Filed: Sep. 3, 1982

Related U.S. Application Data

[63] Continuation-in-part of Ser. No. 126,262, Mar. 3, 1980, abandoned.

[51] Int. Cl.$^3$ .................. A61K 43/00; A61K 49/00
[52] U.S. Cl. .................. 424/1.1; 128/659; 424/9
[58] Field of Search .................. 424/1.1, 9; 128/659

[56] References Cited

U.S. PATENT DOCUMENTS

| | | | |
|---|---|---|---|
| 3,927,193 | 12/1975 | Hansen et al. | 424/1 |
| 4,160,817 | 7/1979 | Bucovaz et al. | 424/1 |
| 4,174,385 | 11/1979 | Reid | 424/1 |
| 4,211,766 | 7/1980 | Björklund | 424/12 |

OTHER PUBLICATIONS

Mack et al., *Europ. J. Cancer, Suppl. 1*, 113 (1978).
Spar, *Sem. Nucl. Med.*, 6, 379 (1976).
Emrich, *Dtsch. Med. Wschr.*, 104, 153 (1979).
Lee et al., *Scand. J. Immunol.*, 8 (Suppl. 8), 485 (1978).
Heyderman, *Scand. J. Immunol.*, 8 (Suppl. 8), 119 (1978).
Goldenberg et al., *N. Eng. J. Med.*, 298, 1384 (1978).
Hawthorne et al., *J. Med. Chem.*, 15, 449 (1972).
Order, *Radiology*, 118, 219 (1976).
Ettinger et al., *Cancer Treat. Rep.*, 63, 131 (1979).
Order et al., *Int. J. Radiation Oncology Biol. Phys.*, 6, 703 (1980).
Ballou et al., *Science*, 206, 844 (1979).
Pressman, *Cancer Res.*, 40, 2960 (1980).
Bale et al., *Cancer Res.*, 40, 2965, (1980).
Order et al., *Cancer Res.*, 40, 3001 (1980).
McIntire et al., *Cancer Res.*, 40, 3083 (1980).

*Primary Examiner*—Christine M. Nucker
*Attorney, Agent, or Firm*—Millen & White

[57] ABSTRACT

Improved methods are provided for using radiolabeled antibodies to tumor cell surface antigens to locate, diagnose and stage tumors having such antigens on their cell surfaces by external photoscanning, whereby significantly increased resolution, convenience and/or efficiency of operation may be achieved. A method is provided for using highly specific radiolabeled antibodies to cell surface antigens for tumor therapy. Radiolabeled antibodies and injectable compositions containing them are provided for use in the method of the invention.

28 Claims, No Drawings

TUMOR LOCALIZATION AND THERAPY WITH LABELED ANTIBODIES TO CELL SURFACE ANTIGENS

CROSS REFERENCE TO RELATED APPLICATION

This application is a continuation-in-part of copending application U.S. Ser. No. 126,262, filed Mar. 3, 1980 now abandoned, the disclosure of which is incorporated herein by reference.

BACKGROUND OF THE INVENTION

It is known that radiolabeled antibodies to carcinoembryonic antigen (CEA) can be used to localize tumors. U.S. Pat. No. 3,927,193, to Hansen et al, discloses such a method, but provides examples of its use only in animals. The method described in this patent does not explain how tumors may be visualized in a situation where radio-activity is also present in other sites of the body, such as blood, other body fluids and certain tissues, particularly heart and liver, which can prevent precise discrimination of the radioactivity associated with the sites of tumor. This reference also teaches that the anti-CEA antibody should not be labeled to a degree which might interfere with its specificity, a limitation which was not questioned in the later references discussed below. However, this limits the resolution of the method and requires larger quantities of antibody for image detection.

Early clinical studies reported by Reif et al, *J. Surg. Oncol.*, 6, 133 (1974) and Mach et al, *Europ. J. Cancer, Suppl.* 1, 113 (1978) failed to show tumorlocalization in humans with radioactive anti-CEA antibodies.

Goldenberg et al, in an article in the *New Engl. J. Med.*, 298, 1384 (1978), reported success in clinical trials of tumor detection and localization by scintillation scanning of patients receiving radiolabeled antibodies to CEA. In that reference, it was noted that there was a problem in both animal and human studies in distinguishing specific radioantibody activity from bloodpool background activity, and that special scanner subtraction techniques with other radionuclides were considered essential for unequivocal tumor localization using this method. The antibody preparation used in the reference was 70% immunoreactive with CEA. The reference further notes that the absence of CEA in normal hamster tissues precludes extrapolation to man, in whom the antigen usually circulates in increased levels in patients with cancer, and is present in lesser quantities in certain normal tissues. The subtraction technique used to permit localization using this scintigraphic method involved injection of Tc-99m-pertechnetate and Tc-99m-labeled human serum albumin prior to each imaging scan. The data obtained were stored in a minicomputer, capable of generating digital images of the labeled antibody alone, the Tc-99m labeled species together, and sums and differences of these various values. However, even this successful tumor localization and detection process had certain disadvantages which limited its resolution, its efficiency and its practicability. The subtraction technique involved the use of a different radionuclide attached to a carrier having kinetics of transport and distribution different from the labeled specific antibody. In addition, the background-compensating material had to be injected prior to each photoscan, which exposed the patient to increased levels of radioactivity and discomfort.

CEA is considered to be primarily a cell-surface antigen, as reported by Heyderman, *Scand. J. Immunol.*, 8, Suppl. 8, 119 (1978), and many others. However, tumor localization using antibodies to cell surface antigens has hitherto been limited to anti-CEA antibodies. Related applications Ser. Nos. 126,261 and 126,263 (now U.S. Pat. No. 4,331,647), both filed Mar. 3, 1980, the disclosures of which are also incorporated herein by reference, disclose tumor localization with labeled antibodies to intracellular tumor associated antigens and with labeled antibody fragments specific to tumor associated markers, respectively.

Tumor radiotherapy using antibodies has been suggested by many, and an indication of its success in a single multimodal therapeutic clinical use was reported by Ettinger et al., *Cancer Treat. Rep.*, 63, 131 (1979). The use of boron-labeled antibodies in therapy was reported by Hawthorne et al., *J. Med. Chem.*, 15, 449 (1972), but the combined incorporation of boron and a radioisotope for localization and therapy was not suggested.

A need continues to exist for methods of tumor detection and localization using cell-surface antigens which are not confined to the use of antibodies to CEA, which do not require repeated injection of background-compensating material for a subtraction technique, which are adaptable to both diagnosis and therapy, which have high reliability and high resolution, which ideally are capable of detecting and locating more than one type of tumor or tumor cells using a single injection, and which avoid other disadvantages of the prior art methods.

OBJECTS OF THE INVENTION

Accordingly, it is an object of the present invention to provide a method of tumor localization and detection which achieves high resolution without the necessity of repeated injection of other radioactive material for computer-assisted subtraction of background activity.

It is a further object of the present invention to provide a method of tumor localization and detection which achieves high resolution and which uses antibodies to cell surface tumor-associated marker substances.

Another object of the present invention is to provide a composition useful in the present method.

Still another object of the present invention is to provide a method of tumor radiotherapy wherein a radio-therapeutically effective radioisotope is concentrated at the site of tumor growth by virtue of its attachment to an antibody which is highly specific to a cell surface tumor-associated marker.

Yet a further object of this invention is to provide a method of tumor therapy wherein thermal neutrons excite a boron-10 isotope-containing antibody to a cell surface marker, which has been localized by detection of an attached radioisotope label.

Upon further study of the specification and appended claims, further objects and advantages of this invention will become apparent to those skilled in the art.

SUMMARY OF THE INVENTION

The foregoing objects are achieved by providing a method for detecting and localizing a tumor having on its cell surface a tumor-associated or tumor-specific antigen, which comprises injecting a human subject parenterally with an antibody specific to said antigen and radiolabeled with a pharmacologically inert radioisotope capable of detection using a photoscanning device, and with indifferent immunoglobulin from the same or different species as that used to prepare said specific antibody, said indifferent immunoglobulin being radiolabeled with a different pharmacologically inert radioisotope emitting at an energy capable of independent detection using said photoscanning device, the radiolabeling being so effected that the kinetics and distribution of the radiolabeled specific antibody and indifferent immunoglobulin in said subject are substantially the same during the time period required for scanning; and scanning the subject with said photo-scanning device, the level of activity of the labeled indifferent immunoglobulin being used to determine the distribution of background activity due to non-targeted specific antibody, said background activity being subtracted from the total activity of specific antibody, whereby the activity of substantially only the targeted tumor-localized specific antibody is determined and said tumor is thereby detected and localized.

An injectable composition suitable for use in the foregoing method is provided, as are a method of tumor radiotherapy using radiolabeled marker-specific tumor-associated antibodies.

DETAILED DISCUSSION

The antibodies used in the present invention are specific to tumor-associated cell surface antigens. The term cell surface antigen is being used here to refer to an antigen of the plasma membrane proper and to any part of the cell periphery, including the so-called "fuzzy coat" and extracellular matrix. Permeability studies and electron microscopy have established the existence of a lipoprotein barrier, the cell membrane, also referred to as plasma membrane or plasmalemma, which is often synonymous with the cell surface. However, in referring to the tumor cell surface herein, the entire surface region and/or periphery of the cell is included, since it is still a difficult task to define the cell surface.

Most of the antigens demonstrated on the surface of cells have been chemically defined as polysaccharides, glycoproteins, glycolipids, or proteins, but other chemical species, such as proteoglycans, may also be involved. Glycosphingolipids and glycoproteins are recognized as integral components of the cell surface membranes as disclosed by, e.g., Singer et al., *Science*, 5, 188 (1972).

Yogeeswaren, in "Cancer Markers-Diagnostic and Developmental Significance", Sell, ed., p. 371 (Humana Press, Clifton, N.J., 1980) has classified tumor-associated cell surface antigens into three groups: (1) oncofetal antigens; (2) viral protein antigens specific for virus transformation; and (3) other protein antigens induced by chemical carcinogens, by viruses, or during "spontaneous" transformation. Methods of restricting the formation of antibodies to human cell surface antigens were summarized in "Monoclonal Antibodies-Hybridomas: A New Dimension in Biological Analyses", Kennett et al., eds., p. 155 (Plenum Press, New York and London, 1980). Such methods included; "Immunization with membrane fractions containing a limited number of membrane components; immunization with one cell type coated with antibodies made against another cell type; immunization with solubilized cell membrane that has been passed through an affinity column to remove immunodominant antigens; immunization with mouse x human hybrids having a few human chromosomes and thus expressing a limited number of human antigens; and immunization with cell-culture supernatant containing a restricted selection of cell-surface antigens, which are shed or secreted and remain stable in significant amounts" (p. 158).

In addition, the monoclonal antibody (hybridoma) technique, originally described by G. Köhler and C. Milstein, *Nature*, 256, 495 (1975), and embodied in U.S. Pat. No. 4,172,124 to Koprowski, using whole tumor cells for immunization, is a useful method for identifying antigens on the cell surface of tumors. Some of these antigens are proteins, and others are of a different chemical nature, such as glycolipids, gangliosides, or proteoglycans. See, e.g., Woodbury et al., *Int. J. Cancer*, 27, 145 (1981); Woodbury et al., *Proc. Natl. Acad. Sci. USA*, 77, 2183 (1980); Loop et al., *Int. J. Cancer*, 27, 775 (1981); Mitchell et al., *Proc. Natl. Acad. Sci. USA*, 77, 7287 (1980); Dippold et al., *Proc. Natl. Acad. Sci. USA*, 77, 6114 (1980); Yeh et al., *Int. J. Cancer*, 9, 269 (1982); Bumol et al., *Proc. Natl. Acad. Sci. USA*, 9, 1245 (1982); Reid, U.S. Pat. No. 4,174,385. These methods of identifying and isolating cell surface antigens are illustrative of techniques in use, and are thus not intended to be all-inclusive.

Other useful methods include antibody affinity chromatography and lectin affinity chromatography, the latter being especially useful for the isolation of surface glycoproteins. Traditional methods of isolating and studying components of cell membranes involve homogenization and fractionation. These methods have been reviewed by DePierre et al., *J. Cell Biol.*, 56, 275 (1973); Graham, in "New Techniques in Biophysics and Cell Biology", Vol. 2, Pain et al., eds., pp. 1-42 (Wiley, London, 1975); and Warren et al., in "Fundamental Techniques in Virology", Habel et al., eds., p. 66 (Academic Press, New York 1969).

Numerous solubilization and extraction techniques have been employed to isolate cell membrane antigens, and for the most part these are not specific, i.e., they isolate a mixture of membrane components. Kahan, in "Methods of Cancer Research", Vol. IX, Busch, ed., p. 283-338 (Academic PRess, New York, 1973) has described a number of extraction methods involving the cleavage of covalent bonds or the dissociation of non-covalent forces. In order to detect the antigens isolated from membranes once the appropriate antibodies are available, various serological tests have been used, such as cytotoxicity, mixed hemadsorption, immunofluorescence and/or other immunohistochemical staining methods, immunoelectron microscopy, paired radioiodine-labeled antibody technique, or isotopic antiglobulin technique. A discussion of these methods is given by Ting et al., in "New Techniques in Biophysics and Cell Biology", Vol. 2, Pain et al., eds., pp. 159-190 (Wiley, London 1975).

The preferred method currently for identifying cell surface antigens of cancer cells is the monoclonal antibody (hybridoma) technique originally described by Köhler and Milstein, *loc. cit.*, using either membrane fractions, membrane isolates, or whole cells as immunogens in animal systems, or by the use of lymphocytes derived from cancer patients to generate human monoclonal antibodies, as described by Wunderlich et al., *Eur. J. Cancer Clin. Oncol.*, 17, 719 (1981), and by Schlom et al., *Proc. Natl. Acad. Sci. USA*, 77 6841 (1980).

Antibodies against tumor associated cell surface antigens prepared and/or isolated by any of the foregoing processes and their equivalents can be radiolabeled and used in the present method and composition.

Some cell surface components of cancer cells are common to normal cells and others are either qualitatively distinct for or quantitatively increased in tumor cells. Cell surface components common to both normal and malignant cells include, e.g., various kinds of receptors (e.g., certain hormone receptors), histocompatibility antigens, blood group antigens, and differentiation antigens. Receptors include, e.g., sheep erythrocyte receptor, hormone receptors, e.g., estrogen receptor and the like, transferrin receptor,, Fc immunoglobulin receptor, nerve growth factor receptor, and the like. Blood group antigens include, e.g., the P determinant and M and N precursor ("T antigen"). Examples of differentiation antigens include surface immunoglobulin, and onco-neural antigens. Examples of histocompatibility antigens include HLA-A, HLA-B, HLA-DR (Ia-like). In cases where the cell-surface antigen is qualitatively distinct for cancer cells or quantitatively increased in cancer as compared to non-cancer tissues such cell surface markers will be useful as targets for localizing antibodies.

Antigens that are more restricted to tumor cells include, e.g., inappropriately (ectopically) expressed normal antigens, modified normal antigens, and neoantigens, such as embryonic and fetal antigens, viral antigens, and tumor-specific (or tumor-associated) antigens. Examples of embryonic and fetal antigens include, fetal onco-neural antigens, onco-fetal antigens, melanoma antigens, colorectal cancer antigens, lung cancer antigens, breast cancer antigens and the like. An example of a virus-associated antigen is the viral capsid antigen of Epstein-Barr virus.

Examples of tumor-specific or tumor-associated antigens include CEA, melanoma cell surface antigens, breast cancer cell surface antigens, lung cancer cell surface antigens, colorectal cancer cell surface antigens, gastric cancer cell surface antigens, pancreatic cancer cell surface antigens, glioma cell surface antigens, common sarcoma cell surface antigens, gastrointestinal cancer cell surface antigens, brain tumor cell surface antigens, esophageal cancer cell surface antigens, common epithelial cancer cell surface antigens, osteosarcoma cell surface antigens, fibrosarcoma cell surface antigens, urinary bladder cancer cell surface antigens, prostatic cancer cell surface antigens, renal cancer cell surface antigens, ovarian cancer cell surface antigens, testicular cancer cell surface antigens, endometrial cancer cell surface antigens, cervical cancer cell surface antigens, Hodgkin's disease cell surface antigens, lymphoma cell surface antigens, leukemic cell surface antigens, trophoblastic tumor cell surface antigens, and the like.

Tumor-specific antigens, by the strictest definition, are not present on normal cells during any stage of development or differentiation. These may result from mutation of structural genes, abnormal gene transcription or translation, abnormal post-translational modification of proteins, derepression of normally repressed genes, or insertion of genes from other cells or organisms ("transfection"). Since only about 1000 gene products have been identified for the approximately 1 million genes in mammalian cells, new tumor-associated antigens will probably be previously undefined normal gene products. An antigen need not be tumor-specific in the strictest sense to be useful as a target for localizing antibodies used for detection or therapy. For example, an inappropriate receptor may serve as a selective target for antibodies used for cancer detection or therapy.

Marker-specific antibodies may be produced by conventional methods well known in the art. Normally, an animal, preferably a rodent, a rabbit, or more preferably a goat or primate, is challenged with a tumor-associated marker substance, to which its immune system reacts by producing specific antibodies to these markers.

Occasionally, a sub-unit or other antigenic cleavage product of a tumor surface marker can be used advantageously to raise antibodies having higher tumor specificity and reduced crossreactivity to non-tumor substances. The animal is bled, the immunoglobulin fraction of the blood is isolated, and the specific immunoglobulin isolated by a variety of conventional separation techniques, preferably including one or more affinity chromotography purification steps. Suitable such general methods for raising antibodies specific to tumor-associated marker substances are disclosed *inter alia* in "Immunodiagnosis of Cancer", Herberman et al., Eds. (Marcel Dekker, Inc., New York and Basel, 1979) and "Tumor Markers", Sell, Ed. (Humana Press, Clifton, N.J., 1980).

Antibodies produced by the foregoing conventional techniques are normally mixtures of antibodies, a certain proportion of which are specific but generally containing a variable proportion of antibodies which are cross-reactive with non-tumor associated or other antigens. Antibodies purified by repeated affinity chromatography using bound antigens with which some components of the antibody mixture are cross-reactive, as well as passage through a column containing bound purified antigen, have a high specific immunoreactivity, often approaching or even exceeding 70%, and a cross-reactivity with non-tumor associated antigens or other antigens of less than 15%. These antibodies are considered substantially mono-specific to the antigen to which they have been raised, and are preferably used in the present invention.

It is particularly advantageous to use antibodies having a high marker-specific immunoreactivity for tumor localization. High specificity means that a high proportion of the labeled antibody will be targeted at tumor sites and a small proportion will be distributed in a non-targeted manner. A smaller quantity of labeled antibody can therefore be used, reducing the subject's exposure to radiation, and the lower level of background radiation due to non-targeted antibody will improve resolution. This in turn means that smaller tumors may be detected that are often difficult or impossible to detect by any other procedure.

Highly specific monoclonal antibodies can be produced by hybridization techniques. Such antibodies normally require little or no purification and normally have a specific immunoreactivity of at least 75%, with specificities of more than 95% in certain cases. Such monoclonal, hybridoma-derived antibodies are also preferred for use in the present invention. Other techniques for producing monoclonal antibodies can also be used, as noted above.

Monoclonal antibodies from the immunoglobulin G(IgG) fraction are obtained by the present method, and are used for tumor detection, localization and therapy according to this invention. The IgM monoclonal antibodies of Koprowski, U.S. Pat. No. 4,172,124, are unsuitable for use in the present method.

Antibodies may be labeled by any of several techniques known to the art. Among the radioisotopes used, gamma-emitters, positron-emitters, x-ray-emitters and fluorescence-emitters are suitable for localization and/or therapy, while beta-emitters and alpha-emitters may also be used for therapy, alpha-emitters being preferable. Suitable radioisotopes for labeling antibodies and/or indifferent IgG include Iodine-131, Iodine-123, Iodine-126, Iodine-133, Bromine-77, Indium-111, Indium-113m, Gallium-67, Gallium-68, Ruthenium-95, Ruthenium-97, Ruthenium-103, Ruthenium-105, Mercury 197, Mercury-203, Rhenium-99m, Rhenium-105, Rhenium-101, Scandium-47, Tellurium-121m, Tellurium-112m, Tellurium-125m, Thulium-165, Thulium-167, Thulium-168, Technetium-99m and Fluorine-18. The halogens can be used more or less interchangeably as labels since halogen-labeled antibodies and/or normal immunoglobulins would have substantially the same kinetics and distribution and similar metabolism. Preferably the radioisotope will emit in the 10-5,000 kev range, more preferably 100-500 kev.

A wide range of labeling techniques are disclosed in Feteanu, "Labeled Antibodies in Biology and Medicine", pages 214-309 (McGraw-Hill Int. Book Co., New York et al, 1978). A preferred technique for labeling antibodies involves labeling with either Iodine-131 (I-131) or Iodine-123 (I-123) using an oxidative procedure wherein a mixture of radioactive potassium or sodium iodide and the antibody is treated with chloramine-T, e.g., as reported by Greenwood et al, *Biochem. J.*, 89, 114 (1963) and modified by McConahey et al, *Int. Arch. Allergy Appl. Immunol.*, 29, 185 (1969). This results in direct substitution of iodine atoms for hydrogen atoms on the antibody molecule, presumably on tyrosine residues, possibly also on tryptophan and even on phenylalanine residues, depending on the proportions of reagents and the reaction conditions.

In general, it is desirable to introduce as high a proportion of radiolabel as possible into the antibody molecule without destroying its immunospecificity. For example, while the vast majority of investigators had considered that introduction by direct substitution of more than from 1.5 to 2 iodine atoms per antibody molecule is disadvantageous, it has now been found that the introduction by direct substitution of at least 2.5 and preferably an average of from 3 to 10 iodine atoms per antibody molecule is advantageous. This is especially the case where the antibody is highly marker specific i.e., having a marker-specific immunoreactivity of at least 70%, preferably at least 80%, and a cross-reactivity of less than 15%, preferably less than 10%, prior to labeling. In this case, even a reduction of the antibody specificity of from 5 to 33% as a consequence of high labeling is outweighed by the advantage of high activity, permitting the use of substantially smaller quantities of labeled antibody.

Radioactive metals with half-lives ranging from 1 hour to 3.5 days are available for conjugation to antibodies such as scandium-47 (3.4 days), gallium-67 (2.8 days), gallium-68 (68 minutes), technetium-99m (6 hours), and indium-111 (3.2 days), of which gallium-67, technetium-99m, and indium-111 are preferable for gamma camera imaging, gallium-68 is preferable for positron emission tomography, and scandium-47 (and other alpha-emitting radionuclides) are preferable for tumor therapy.

A useful method of labeling antibodies with such radiometals is by means of a bifunctional chelating agent, such as diethylenetriaminepentaacetic acid (DTPA), as described, for example, by Khaw et al. (Science 209, 295, 1980) for In-111 and Tc-99m, and later by Scheinberg et al. (*Science* 215,1511, 1982). Other chelating agents may also be used, but the 1-(p-carboxymethoxybenzyl)EDTA and the carboxycarbonic anhydride of DTPA are advantageous because their use permits conjugation without affecting the antibody's immunoreactivity substantially.

Another method for coupling DTPA to proteins is by use of the cyclic anhydride of DTPA, as described by Hnatowich et al. (*Int. J. Appl. Radiat. Isot.* 33, 327, 1982) for labeling of albumin with In-111, but which can be adapted for labeling of antibodies. A suitable method of labeling antibodies with Tc-99m which does not use chelation with DTPA is the pretinning method of Crockford et al., U.S. Pat. No. 4,323,546; also described in "Tumor Imaging. The Radiochemical Detection of Cancer," Burchiel et al., Eds, pp. 111-123 (Masson Publishing USA, New York, 1982).

A preferred method of labeling immunoglobulins with Tc-99m is that described by Wong et al. in *Int. J. Appl. Radiat. Isot.*, 29, 251 (1978) for plasma protein, and recently applied successfully by Wong et al. in *J. Nucl. Med.*, 23, 229, 1982 for labeling antibodies.

In the case of the radiometals conjugated to the specific antibody, it is likewise desirable to introduce as high a proportion of the radiolabel as possible into the antibody molecule without destroying its immunospecificity. Again, even a reduction of the antibody specificity of from 5 to 33% as a consequence of high labeling is outweighed by the advantage of high specific activity, permitting the use of substantially smaller quantities of the labeled antibody and/or effecting a higher sensitivity of the tumor-locating method, on the one hand, or a more effective antitumor therapy, on the other. This reduction in immunospecificity of the highly purified or monoclonal antibody, however, should not so affect the preparation as to alter its *in vivo* biodistribution and metabolism such that the principle of subtraction of the radioactivity of the indifferent immunoglobulin from that of the similarly distributed (with the exception of accretion in the tumor) antitumor antibody is compromised. A further improvement may be achieved by effecting radiolabeling in the presence of the specific antigen, to insure that the antigen binding site on the antibody will be protected. The antigen is separated after labeling.

The foregoing are merely illustrative of the many methods of radiolabeling proteins known to the art. These procedures can also be used in a substantially identical manner for labeling irrelevant (indifferent) immunoglobulin of the same or a different species as that of the antitumor antibody in order to effect the subtraction process disclosed herein for imaging neoplasms.

Mixtures of labeled antibodies specific to different antigens or different epitopes of the same antigen associated with the same or different tumor or tumor cell types may be used. This can enhance detection, localization and/or therapy in certain cases, and can also increase the range of a broad screen for more than one tumor or tumor cell type.

In contrast to earlier known procedures, which permit tumor localization usually only after 24 hours following administration of the radiolabeled specific antibody, the present improved subtraction technique permits tumor detection and localization within less than 24 hours after concurrent administration of radiolabeled specific antibody and radiolabeled normal immunoglobulin. Tumor localization can be achieved as early as two hours after injection of the antibody/immunoglobulin pair, with improved resolution at 6, 12, 18 and 24 hours after administration.

In the reported successful noninvasive radioimmunodetection of cancer in humans of Goldenberg, et al., *N. Engl. J. Med.*, 298, 1384 (1978), a subtraction technique was shown to be necessary for successful localization. However, the subtraction technique used was substantially different from that of the present invention. In the reference process, radioiodinated anti-CEA antibody was injected, and Tc-99m-labeled human serum albumin and Tc-99m-pertechnetate were injected intravenously before each imaging scan. Images were obtained with a gamma-scintillation camera and the data obtained were stored in a minicomputer. The ratio of I-131 activity to Tc-99m-activity in non-target areas provided a standard of comparison for background non-localized antibody activity. This in turn permitted a rough approximation of the level of non-targeted specific antibody activity at other locations, which was then subtracted from the total specific antibody activity to yield a value for the activity of localized, targeted antibody.

Critical to the method of computer-assisted subtraction for more precise tumor imaging by an external radiation detection machine is the substantially similar distribution in the body of the antitumor antibody labeled with one isotope to that of the indifferent immunoglobulin labeled with an isotope of a different energy capable of separate identification by the radiation detection camera and thus permitting the latter to be subtracted from the former. This principle is described in U.S. Serial No. 126,262 and illustrated for anti-CEA antibodies using different radioisotopes of the same element for labeling the specific antibody and the reference indifferent IgG. In the present method, however, the second radionuclide need not be of the same element as that of the one attached to the antitumor antibody (such as I-123 for the indifferent immunoglobulin and I-131 for the antitumor antibody). For example, the antitumor antibody may be labeled with I-131 and the indifferent immunoglobulin with Tc-99m, In-111, or Ga-67; the antitumor antibody may be labeled with In-111 and the indifferent immunoglobulin with Tc-99m; or variations thereof.

The choice of the combination of radionuclides used s determined not only by the imaging qualities of said radionuclides, but further by the stability, chemical and biological integrity, and biodistribution properties of the diversely radiolabeled antibody and immunoglobulin preparations. These can be determined, for example, by assessing the immunoreactivity of the antibody and the antigenicity of the indifferent immunoglobulin by binding properties to the appropriate tumor antigen or anti-immunoglobulin antibody, respectively, these being bound to an affinity column, for example, as described in U.S. Ser. No. 126,262 for I-131 or I-123-labeled antibodies to CEA. The physicochemical integrity of the labeled immunoglobulins can be confirmed by protein electrophoresis or gel filtration procedures, which should show that the majority of the immunoglobulin electrophoreses or chromatographs with the radiolabel.

Finally, and perhaps most important, both labeled preparations, when injected in animals in equivalent amounts of immunoglobulin protein or in amounts reflecting the ratios by which they will be injected in humans, will have similar or virtually identical organ distribution during the period after injection when imaging is to be undertaken, which in humans is up to about 48 hours, preferably less than 24 hours. It has been shown, for example, by Hnatowich et al., *Int. J. Appl. Radiat. Isot.*, 33, 327 1982 that albumin labeled with In-111 using the chemically coupled ligand diethylenetriamine-pentaacetic acid (DTPA) has a substantially similar biodistribution in normal mice at 45 min after injection to albumin labeled with I-125. These three approaches to confirming the integrity and biokinetic similarity of the differently labeled preparations are meant as examples and are not restrictive of methods available for such purposes to one skilled in this technology.

The isotopes used to label the immunoglobulins and the method of this conjugation are only important in this process to the degree that they do not affect the physico-chemical and biological properties of said immunoglobulins, as illustrated above, and thus hinder their similarity in biodistribution (kinetics, clearance, etc.) after injection and during the time frame when imaging is desired (which is also determined by the isotopes' half-lives).

Among the significant advantages of using as a reference substance a molecular species having essentially the same kinetics of binding, distribution and metabolism as the labeled specific antibody are that only a single injection of the reference substance is necessary, increased resolution is achieved, and tumor localization can be achieved in a shorter time. The reference substance in the present method is the corresponding indifferent immunoglobulin G (IgG) from the same or different species as that used to prepare the specific antibody used as the tumor localization agent. The indifferent IgG is radiolabeled with a different radioisotope from that used to label the specific antibody, and which is capable of independent scintigraphic detection. The labeling is so effected that the resultant labeled specific antibody and indifferent IgG have substantially the same kinetics and distribution in the patient during the time period required for scintigraphic scanning and tumor localization.

Further improvement in resolution is achieved by using a highly purified radiolabeled indifferent IgG for the reference substance in the subtraction technique. Normal globulin is a mixture of globulins, some of which may bind to the specific antigen to which the radioactive antibody is directed. Therefore, it is desirable to purify the normal globulin to be used as a subtraction agent so as to remove any reactivity to the specific marker in question, and one such purification method is to adsorb the normal immunoglobulin with the specific antigen, preferably on a solid adsorbent, so that the globulins reacting with the antigen will be retained on the column and the materials passing through will be more suitable for labeling as a non-specific subtraction agent. Monoclonal non-specific immunoglobulin or myeloma protein itself will also have the desired purity for labeling and use as subtraction agents.

The indifferent IgG can be radiolabeled with a different isotope of the same element used to label the specific antibody. Suitable pairs of radioisotopes for this preferred embodiment, one of which may be used for labeling the specific antibody and the other of which is used to label the indifferent IgG, include Iodine-131 and Iodine-123, Indium-111 and Indium-113m; Gallium-67 and Gallium-68; Ruthenium-97 and Ruthenium-103; or Mercury-197 and Mercury-203. Because iodine may be introduced directly by a chemical substitution reaction, and has at least five isotopes which are radioactive and detectable using a photoscanning device, it is conveniently used for radiolabeling both the specific antibody fragment and the indifferent IgG reference for use in the method of the invention. Advantageously, Iodine-123 is used for labeling the normal immunoglobulin. The resultant emissions are separately detectable on two different channels of a gamma-scintillation detector.

The radiolabel is introduced into the indifferent IgG by the same techniques used to label specific antibodies, as discussed above.

The labeled indifferent IgG reference substance is preferably injected concurrently with the labeled specific antibody, although it can be injected earlier or later. A single injection of labeled antibody, preferably together with the reference IgG, is advantageously made for localization.

Photoscanning is effected as described in Goldenberg et al., *New Engl. J. Med.*, 298, 1384 (1978), and references cited therein. The resultant scanning data are conveniently stored in a minicomputer and the aforementioned subtraction procedure is effected to determine the regions of excess accumulation of radiolabeled specific antibody over its ratio to labeled reference immunoglobulin in non-target areas. The level of activity of the reference substance is used to determine the background activity due to non-targeted specific antibody, and this background activity is then subtracted from the total activity of the specific antibody permitting a determination of the activity of substantially only the targeted, tumor-associated antibody.

Further improved resolution can be achieved using a technique reported by Goldenberg, et al., *Proc. Nat. Acad. Sci. USA*, 78, 7754 (1981). These authors used Tc-99m-pertechnetate and Tc-99m-labeled human serum albumin as reference substances which were injected prior to each scan, and I-131-labeled specific antibody. They further refined the subtraction method for certain organs, such as liver, by use of an organ-specific radionuclide (e.g., Tc-99m-sulfur colloid), whereby the organ's image was selectively extracted from the region of interest, and then the Tc-99m radioactivity was subtracted, pixel by pixel, from that of I-131. The organ-specific radio-nuclide was given following the routine examination with Tc-99m-human serum albumin and Tc-99m-pertechnetate as non-target subtraction agents. In other instances, such as for the lungs, selective organ extraction was accomplished by outlining the organ of concern electronically, and then processing according to the standard subtraction method. By this means, greater confidence in identifying tumor-related radioactivity (as compared to non-target background) was achieved.

The values computed for excess localization of specific antibody over reference IgG can be used to generate a related output signal, advantageously a gradation of colors on a color video screen. The photoscanning device can also include computed tomographic capabilities.

This highly efficient subtraction technique with the use of highly monospecific, preferably monoclonal antibodies labeled to give the maximum balance between high activity and acceptable immunospecificity, provides a tumor localization and detection method of significantly improved resolution. The use of the present method permits either continuous, repeated or occasional monitoring of tumor locations. This has particular advantages in conjunction with the diagnosis and staging of tumors prior to surgery. In addition, the method is useful during and after surgery as an indication of the extent to which complete tumor removal has been achieved. In case of metastasis, especially where there has been a proliferation of small, diffuse metastases, the high resolution of the present method permits identification of target areas for post-operative therapy. This can be effected using the therapeutic method of this invention or other known techniques, e.g., chemotherapy, radiation treatments, or multimodal therapies.

Radiolabeled cell surface marker-specific antibodies are effective for tumor therapy. After it has been determined that labeled antibodies are localized at tumor sites in a subject, a higher dose of labeled antibody, generally from 25 to 250 mCi for I-131, and preferably from 50 nCi to 150 mCi per dose, based on a 70 kg patient weight, is injected. Injection may be intravenous, intraarterial, intralymphatic, intrathecal, or intracavitary, and may be repeated. It may be advantageous for some tumor therapies to administer multiple, divided doses of radiolabeled antibody or antibody mixtures, e.g., in the range of 20–120 mCi (70 kg patient), thus providing higher tumoricidal doses without usually effecting a proportional increase in radiation of normal tissues.

A variety of radionuclides are useful for therapy, apd they may be incorporated into the specific antibody by the labeling techniques discussed above. A preferred therapeutically effective radionuclide is I-131, although radionuclides emitting alpha and beta particles and of relatively shorter half-lives are also suitable.

The therapeutic method of this invention also advantageously makes use of highly marker-specific antibody, preferably an antibody which is substantially monospecific, having a marker-specific immunoreactivity of at least 70%, preferably 80%, and a cross-reactivity to other antigens of less than 15%, preferably less than 10%. Monoclonal antibodies are preferred because of their high specificity.

Therapy using radiolabeled marker-specific antibodies is advantageously used as a primary therapeutic treatment, in combination with other therapies, e.g., radiation and chemotherapy, and as an adjunct to surgery. Where there may be small metastases which cannot be surgically removed or which may escape detection, the radiotherapeutic method of the invention provides a potent weapon capable of seeking out and destroying these tumors.

A further aspect of the present invention relates to the use of antibodies containing both a radioisotope label and an addend containing significant numbers of boron atoms, having at least the 20% natural abundance of boron-10 isotope. The boron-containing addend may be introduced by a variety of methods, preferably by coupling the antibody with a boron-rich coupling agent, such as the diazonium ion derived from 1-(4-aminophenyl)-1,2-dicarbaclosododecaborane(12), according to the method of Hawthorne et al., *J. Med. Chem.*, 15, 449 (1972) and/or Mizusawa et al., *Proc. Natl. Acad. Sci USA*, 79, 3011 (1982). The boron-10-containing antibody is then radiolabeled according to one or more of the above procedures to produce an antibody containing both one or more radiolabels for tumor localization and/or therapy and a high content of boron-10 atoms for the absorption of thermal neutrons. Injection of the radiolabeled and boron-labeled antibody, together with labeled reference IgG, is followed by localization of tumors using the method of this invention. The tumors are then irradiated with a well collimated beam of thermal neutrons, which are preferentially absorbed by boron-10 nuclei on the boron-containing addends, and the activated nucleus decays rapidly to lithium-7 and an alpha-particle. These resultant alpha-particles are cytotoxic, and their production in tumor cells kills the cells and causes tumor reduction.

Combination of a boron addend with one or more radiolabels on a highly marker-specific antibody to a tumor cell surface antigen provides for the first time a single agent which functions as a multimodal tumor therapeutic agent. The rapid and specific localization of these doubly labeled antibodies at the site of a tumor permits a rapid and precise definition of the areas where neutron irradiation should be focused. Moreover, as tumor cells are destroyed by the combined effects of radiation from the radiolabel and neutron-activated boron-10 emissions, and the killed tumor cells are eliminated, the progress of the radio-therapeutic treatment may be monitored by measurement of localized, radiolabeled antibody or other tumor detection methods.

The antibodies of the invention are generally administered in the form of injectable compositions. For screening, and for many types of localization and therapy, injection will be intravenous, intraarterial or intrathecal. The injectable antibody solution will be administered into a vein, artery or into the spinal fluid over the course of from 2 minutes to about 1 hour, preferably from 10 minutes to 20 minutes for intravenous or intraarterial infusion. In certain cases, subcutaneous, submucosal, or intracavitary administration is advantageous. Where the tumor is supplied by a known, accessible artery, intraarterial administration is preferred for therapy. The intraarterial route can be used for longer periods of infusion of the preparation, e.g., 24 hours or longer. In addition, intrathecal administration may be used for tumors located in the brain. Subcutaneous, submucosal and intracavitary administration are advantageous for tumors restricted to areas close to particular regions of the skin and/or to particular body cavities.

The subtraction techniques of the present invention can be used to improve and extend the lymphoscintigraphic diagnostic method reported by DeLand et al., *Cancer Res.*, 40, 2997 (1980), which used radiolabeled anti-CEA IgG without subtraction to study lymphatic drainage from tumors. More extensive and distant lymph nodes and channels can be imaged and longer post-injection imaging times are made possible using the present subtraction methods with labeled antibodies to cell surface antigens, together with labeled indifferent IgG.

A typical injectable composition according to the invention contains human serum albumin, about 1 to 500 micrograms of radiolabeled specific antibody per milliliter of buffer, e.g., 0.04 M phosphate buffer, pH 7.4, containing 0.9% NaCl, and a quantity of radiolabeled indifferent IgG roughly equal to the weight of specific antibody is also included. Other conventional pharmaceutically acceptable injection vehicles may be used where indicated, such as for intrathecal, subcutaneous, submucosal, or intracavitary injection as well as for intravenous or intraarterial injection.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Antibodies used in these examples are highly specific, either prepared by conventional immunization followed by complement inactivation, adsorption to remove hemagglutination components and affinity purification against cross-reactive antigens and the specific antigen, or hybridoma-derived monoclonal antibodies.

EXAMPLE 1

Preparation of Labeled Monoclonal Antibody Against Human-Germ-Cell-Cancer Cell-Surface Antigen (a) Monoclonal antibodies recognizing one or more germ cell tumor cell-surface antigens are produced according to the method of Moshakis et al., *Brit. J. Cancer*, 44, 91 (1981). Antibodies are raised in Balb/c mice with a xenografted human malignant teratoma. The spleen cells of the immunized mice are then fused with readily available murine myeloma NS1 cells. Viable antibody-producing hybrid clones are isolated by standard procedures, e.g., those described in Example 2 of U.S. Ser. No. 126,262, and shown to react with the teratoma cells by in vitro assays. Hybrid clones producing a suitable antibody are grown in the ascites form in mice, and this ascitic fluid is later collected and the antibody purified by precipitation with 50% ammonium sulfate and Sephadex G-200 chromatography, resulting in an IgG antibody specific to at least one surface antigen on germ cell tumor cells.

(b) The monoclonal antibody prepared in part (a) is labeled with I-131 by the procedure of Example 1(f) of U.S. Ser. No. 126,262.

EXAMPLE 2

Preparation of Labeled Monoclonal Antibodies Against Cell-surface Antigens of Gastrointestinal Cancer (a) The method of Herlyn et al., *Proc. Natl. Acad. Sci. USA*, 76, 1438 (1979), is adapted to produce monoclonal antibodies of a suitable IgG subclass which recognize a gastrointestinal cancer antigen that is a ganglioside present on the surface of gastrointestinal cancer cells, as reported by Magnani et al., *Science*, 212, 55 (1981). Colonic carcinoma cells, in particular LS-174T cells, from a confluent layer are trypsinized from the surface of the tissue culture flask, washed 3 times in cold phosphate-buffered saline containing 8.0 M NaCl, 0.20 M KCl, 0.2 M $KH_2PO_4$, 1.15 M $Na_2HPO_4$, 0.10 M $CaCl_2$ and 0.10 M $MgCl_2.6H_2O$ (hereinafter PBS), and resuspended ($5 \times 10^7$ cells/ml) in PBS conntaining 2 mM phenylmethylsulfonyl fluoride. The cells are thereafter disrupted with a homogenizer at 4° C., after which the nuclei and debris are removed by centrifugation at $600 \times g$. The supernatant containing the membranes is pelleted at $100,000 \times g$, resuspended in 1 ml of PBS containing 2 mM phenylmethylsulfonyl fluoride, and stored at −70° C. until used.

Balb/c mice are given an initial intraperitoneal injection of the membrane preparation. After 1–3 months, the mice are given intravenous booster injections on three consecutive days of 0.2 ml of the cell membrane suspension. The mice are sacrificed 3 days after the last booster and their spleen cells are fused to the nonsecreting myeloma cell line P3X63Ag8-653, using polyethylene glycol. The remaining steps in the procedure are carried out as in Example 2 of U.S. Ser. No. 126,262, except that the gastrointestinal membrane preparation is used instead of CEA where needed for identification of monoclonal antibodies reacting with the gastrointestinal cancer antigen.

(b) The monoclonal antibody prepared in part (a) is labeled with I-131 using the IODO-GEN™ reagent, 1,3,4,6-tetrachloro-3a,6a-diphenylglycoluril (Pierce Chemical Company, Rockford, Illinois), according to the procedure of Fraker et al., *Biochem. Biophys. Res. Commun.*, 80, 849 (1978). A specific activity of 15–80 Ci/g IgG protein is achieved without effecting the immunoreactivity of the antibody to an unacceptable extent.

(c) The monoclonal antibody prepared in part (a), at a concentration of 5 mg/ml, is treated with a 250-fold molar excess of the carboxycarbonic anhydride of diethylenetriaminepentaacetic acid (DTPA) at a concentration of 0.025 mM, in 100 mM bicarbonate at pH 7.5. The anhydride is prepared by the method of Krejcarek et al., *Biochem. Biophys Res. Commun.*, 77, 581 (1977). After extensive dialysis against metal-free NaCl, the DTPAtreated antibody, at a concentration of 2 mg/ml, is labeled with 1 mCi indium-111, as $InCl_3$, in 50 mM citrate at pH 3.6. Free In-111 is removed by ion-exchange chromatography, folowed by dialysis against buffered NaCl at pH 6.6, according to the procedure of Scheinberg et al., *Science*, 215, 1511 (1982).

EXAMPLE 3

Preparation of Labeled Monoclonal Antibodies Against Breast Cancer Cell-surface Antigens (a) Balb/c mice are immunized with live whole human breast cancer cells according to the procedure of Example 2. The mammary cancer cell-surface antigen-recognizing antibody IgG is purified from ascitic fluid of pristaneprimed Balb/c mice inoculated intraperitoneally with 10 million hybridoma cells. First, the ascitic fluid is centrifuged at 10,000×g for 10 min, the supernatant adjusted to pH 7.5 using 0.1 M Tris-HCl buffer, and the immunoglobulin precipitated by adding an equal volume of saturated ammonium sulfate. After incubation for 1 hour at 4° C., the immunoglobulin is pelleted by centrifugation at 10,000 ×g for 10 min, reconstituted in 5 ml of 5 mM sodium phosphate buffer at pH 7.5, dialyzed against 5 mM sodium phosphate buffer, and applied to a DE 52 (15 ml) ion-exchange column. The antibody is eluted with a salt gradient of 5–100 mM sodium phosphate at pH 7.5, collecting 2-ml fractions and determining the absorbance at 280 nm. The IgG fractions reacting in solid-phase radioimmunoassay against extracts of human mammary cancer are pooled and dialyzed against PBS, and then further purified by gel filtration through Ultrogel AcA44 in PBS.

(b) The monoclonal antibody prepared in part (a) is labeled with I-131 using the procedure of Example 1(f) of U.S. Ser. No. 126,262, resulting in a specific activity of 20–40 Ci/g IgG protein.

EXAMPLE 4

Preparation of Labeled Monoclonal Antibodies Against Cell-surface Antigens of Human Malignant Melanoma Cells (a) Hybridoma-derived monoclonal antibodies against cell-surface antigens of human malignant melanoma cells are prepared according to the procedure of Example 3, except that the live whole human breast cancer cells are replaced by a membrane-enriched fraction of human melanoma cells obtained from fresh human tumor specimens.

(b) The monoclonal antibody prepared in part (a) is labeled with I-131 according to the procedure of Example 1(f) of U.S. Ser. No. 126,262.

EXAMPLE 5

Preparation of Labeled Indifferent IgG (a) Myeloma IgG derived from MOPC-21 murine myeloma, commercially available from, e.g., Litton Bionetics, is labeled with technetium-99m according to the procedure of Wong et al., *Int. J. Appl. Rad. Isot.*, 29, 251 (1978). A 60 mCi sample of sodium Tc-99mpertechnetate is reduced by addition of 0.5 ml of a solution of 0.1 mg $SnCl_2$ in 0.05 N HCl solution. The mixture (pH 1.8) is incubated at room temperature for 10 min, then readjusted to pH 7.4 with 0.75 ml trisodium citrate/NaOH solution (pH 12.4). Then, 1 ml of a solution containing 4 mg of the myeloma IgG in Sorenson phosphate buffer (pH 7.4) is added by very slow injection with gentle swirling into the reaction vial, and incubated for 30 min at room temperature. The radionuclide is incorporated into the protein to the extent of about 98%, as shown by protein electrophoresis, and there is no appreciable reduction of the integrity of the indifferent immunoglobulin.

(b) The myeloma IgG from MOPC-21 murine myeloma is labeled with Indium-111 in the same way that the specific immunoglobulin was labeled in Example 2(c).

EXAMPLE 6

Preparation of Radiolabeled Boron-containinq Specific Antibodies

The monoclonal antibody against breast cancer cell-surface antigens prepared according to Example 3(a) is reacted with a 20-fold molar excess of the diazonium salt of 1-(4-aminophenyl)-1,2-dicarba-closododecaborane(12) having a natural abundance of Boron-10 (20%), using the procedure of Hawthorne et al., *J. Med. Chem.*, 15, 449 (1972) and/or the procedure of Mizusawa et al., *Proc. Natl. Acad. Sci. USA*, 79, 3011 (1982). This results in conjugation of at least five carborane moieties, or at least 50 boron atoms containing at least 10 Boron-10 atoms, per IgG molecule, without appreciably affecting antibody protein content or immunoreactivity. The boronconjugated antibody is radioiodonated according to the procedure of Example 3(b).

EXAMPLE 7

Quality Control Procedures for Radiolabeled Antibodies Against Cell-surface Cancer-associated Antigens (a) Gel filtration chromatography on Sephacryl S-300

1. The labeled antibody of each of the preceding Examples is diluted 1:1000 in PBS, pH 7.2, containing 0.5% human serum albumin (HSA).

2. An aliquot of 400 $\mu$l (containing about 16.7 ng protein) of the diluted labeled antibody is added to 1.6 ml PBS, pH 7.2, containing 5 mg indifferent IgG (preferably of the same species as the antibody) which acts as a "carrier" protein, and applied to a 2.6×100-cm column of Sephacryl S-300 that has been equilibrated with PBS, pH 7.2, containing 0.02% sodium azide.

3. The column is eluted with the same buffer, at a flow rate of 50 ml/hr, and fractions of 5.0 ml are collected.

4. The optical density at a wavelength of 280 nm of the column eluents is monitored and recorded. The recorder is equipped with an event-marker which marks the recorded absorbance corresponding with the appropriate fractions.

5. A total of about 130 fractions are collected and the radionuclide content (cpm) in each one is determined by means of a gamma scintillation counter.

6. The chromatographic distribution pattern of the labeled antibody is compared to that of the "carrier" indifferent, unlabeled IgG by plotting the cpm content in each fraction on the chart of the absorbance at 280 nm values.

This procedure allows a determination of the amount of radionuclide conjugated to the antibody IgG. A determination can also be made by electrophoresis of the sample, compared to electrophoresis of the unlabeled immunoglobulin.

(b) Affinity-chromatography on the appropriate antigen-immunoadsorbent

1. The appropriate antigen adsorbent, made by coupling the antigen extract to which the antibody is reactive, e.g., the gastrointestinal cancer antigen of Example 2, to Sepharose 4B by the cyanogen bromide method, as described in Example 1(d) of U.S. Ser. No. 126,262 for CEA affinity chromatography, which has the capacity to bind more than 10 ng antibody, is packed into a 10 ml plastic syringe equipped with a porous disc at the bottom. Another disc is fitted on the top of the immunoadsorbent gel, and a valve is installed on the outlet of the mini-column.

2. The immunoadsorbent is equilibrated with 0.1 M sodium phosphate, pH 7.0, containing 1% indifferent serum of the species of the antibody (e.g., mouse) and 0.02% sodium azide.

3. A volume of 200 μl of the 1:1000 dilution of the labeled antibody is applied to the column and washed into the immunoadsorbent with addition of 200 μl of the phosphate buffer.

4. The flow is stopped and the antibody is allowed to react with the immunoadsorbent for 30 min at room temperature.

5. At the end of this incubation period the column is eluted with 10 ml of the phosphate buffer, and the eluent is collected in a 16×150-mm test tube, and this is designated as Fraction #1.

6. Subsequently the column is eluted with 10 ml 6 M guanidine hydrochloride made in sodium phosphate, pH 7.0, and the eluent is collected in a second 16×150-mm test tube, designated as Fraction #2.

7. The column is then washed with 10 ml of the initial phosphate buffer and the eluent is collected in a third 16×150-mm test tube, designated Fraction #3.

8. A reference sample is prepared by diluting 200 μl of the diluted labeled antibody to a final volume of 10 ml with the phosphate buffer, designated as "Total Counts Applied" to the immunoadsorbent.

9. The cpm content in each of the three fractions and reference tube is determined.

10. The following calculations are made:

% Recovery:     i.

$$\frac{[cpm \text{ Fraction } \#1] + [cpm \text{ Fractions } \#2 \text{ and } \#3]}{\text{"Total Counts Applied"}} \times 100$$

% Non-reactive IgG:     ii.

$$\frac{cpm \text{ Fraction } \#1}{[cpm \text{ Fraction } \#1] + [cpm \text{ Fractions } \#2 \text{ and } \#3]} \times 100$$

% Immunoreactive IgG:     iii.

$$\frac{[cpm \text{ Fractions } \#2 \text{ and } \#3]}{[cpm \text{ Fraction } \#1] + [cpm \text{ Fractions } \#2 \text{ and } \#3]} \times 100$$

(c) Solid-phase radioassay

The immunoreactivity of the labeled antibody can also be determined by a solid-phase radioassay, using cell extracts of the human cancer cells containing the surface antigen in question (e.g., mammary cancer cells for the monoclonal antibody recognizing a mammary cancer surface antigen, as in Example 3). Five μl (in 50 μl) of the cell extracts are added to each well of 96-well microtiter polyvinyl plates and left to dry. The microtiter wells are treated with 100 μl of 5% bovine serum albumin (BSA) in PBS and incubated for 1 hr at 37° C., in order to reduce nonspecific protein absorption. The BSA is removed and varying amounts of the radiolabeled antibody (in 50 μl) are added. After incubation for 1 hr at 37° C., the unbound immunoglobulin is removed by washing the plates with 1% BSA in PBS. The plates are incubated for an additional hour and then washed extensively with 1% BSA in PBS. The bound counts are then detected by cutting the individual wells from the plate and measuring the radioactivity in a gamma scintillation counter. These results are then compared to identical plates in which an identically labeled indifferent immunoglobulin of the same species (e.g., mouse serum IgG or MOPC-21 IgG) is used instead of the specific antibody, thus allowing a determination of the % of radiolabeled antibody immunoreactive with the cancer surface antigen of interest.

(d) Tumor localization in vivo in human tumor xenografts

Athymic, nude mice (nu/nu on a Balb/c background) are grafted subcutaneously with a suitable number (e.g., $2 \times 10^6$) of human cancer cells of the type desired for radiolabeled antibody localization. The mice can also be grafted with control, different human cancer cells lacking the appropriate cell surface antigen, in order to demonstrate selective antibody localization only in the suitable, surface-antigen-containing human tumors. The radiolabeled antibody or indifferent immunoglobulin (2 to 80 μg) is injected intracardially or intraperitoneally after tumors are established, usually when these measure 0.4–1.0 cm in diameter. When a radioiodine label is used, the drinking water is supplemented with 0.1% v/v NaI throughout the experiments, commencing about 2 days before injection of the radioiodinated antibody or indifferent IgG. One to five days later (depending on radionuclides used), the mice are sacrificed and dissected, the tumors, visceral organs, muscle, bone, blood samples and residual carcass are weighed and assayed for radioactivity by a gamma scintillation counter. In order to assess specific uptake of the radiolabeled antibody in the tumor, a similar quantity of indifferent IgG of the same or a different species, or, preferably, the myeloma MOPC-21 IgG in the case of murine monoclonal antibodies, is labeled with an isotope of different energy and capable of separation from that of the isotope used to label the specific antibody (e.g., I-131 for antibody and I-125 for indifferent IgG; I-131 for antibody and Tc-99m for indifferent IgG), and injected simultaneously in equivalent amounts of IgG protein with the specific radiolabeled antibody preparation. After weighing the organs and assaying for radioactivity, the results are expressed as a percentage of injected radioactivity/g tissue and/or as a ratio of injected radioactivity/g tumor to that of a particular reference tissue or to blood (tumor/nontumor and tumor/blood ratios). When the mice receive dual labeled immunoglobulins and antibody simultaneously, a "localization ratio" is calculated for each organ by the formula, $$\frac{\text{tissue:blood ratio labeled antibody}}{\text{tissue:blood ratio indifferent immunoglobulin}}$$

This procedure will show preferential uptake of labeled specific antibody in the tumor and substantially the same uptake of specific and indifferent IgG in normal organs.

(e) In vivo kinetics and distribution of dual labeled antibody and indifferent immunoglobulin preparations injected simultaneously The similarity in kinetics, metabolism, and organ distribution of antibody and indifferent immunoglobulin, each labeled with a different isotope capable of detection and discrimination from one another by a gamma camera, for the time period of imaging, preferably within 24 hours but, with certain radionuclide combinations, up to at least 48 hours, can be evaluated prior to clinical studies by similar procedures to those described in part (d). However, it is advantageous that the mice (or another animal species) not bear the appropriate tumor, or bear another control tumor which should not accrete the antibody or indifferent immunoglobulin significantly. The mice are then sacrificed at regular intervals (e.g., every 4–8 hours) during a 24–48 hr period and the organs dissected and weighed, and assayed for radioactivity, as described in part (d). The percentage of injected radioactivity/g tissue and the tissue:blood ratio for the two radiolabeled preparations should be virtually equal or, in the formula of part (d), almost 1, as long as the kinetics and distribution of the antibody and indifferent immunoglobulin preparations labeled with two different radionuclides are essentially identical for the time period desired for imaging experiments.

EXAMPLE 8

Quality Control Procedure for Radiolabeled Indifferent IgG (a) Gel filtration chromatography on Sephacryl S-300

The procedure of Example 7(a) is followed, except that indifferent IgG is used instead of antigen-specific IgG.

(b) Affinity-chromatography on the appropriate antigen-immunoadsorbent

The procedure of Example 7(b) is followed with the exception that the immunoadsorbent is made of antibody against the species IgG of the indifferent immunoglobulin, such as goat anti-mouse IgG for the indifferent murine IgG or donkey anti-goat IgG for indifferent goat IgG, coupled to Sepharose 4B.

EXAMPLE 9

Preparation of Injectable Compositions

Sterile, pyrogen-free solutions are prepared as shown.

(a) A sterile solution containing, per ml:
(1) 34 mg Human Serum Albumin (HSA) (1%, USP, Parke-Davis)
(2) 0.04 M phosphate buffer, pH 7.4 (Bioware)
(3) 0.9% NaCl
(4) 10 μg I-131-anti-CEA IgG (goat) prepared according to Example 1 of U.S. Ser. No. 126,262, having an average of about 5 atoms of iodine/molecule, and a specific activity of 20–40 Ci/g IgG protein.

The labeled antibody is stored in a solution of (1), (2) and (3) at a concentration of 20 μg/ml and diluted with an equal volume of 1% HSA in PBS to prepare this solution.

(b) A sterile solution according to the procedure of part (a) except that the antibody is the I-131-anti-CEA IgG (monoclonal) prepared according to Example 2 of U.S. Ser. No. 126,262, stored in 1% HSA in PBS at a concentration of 20 μg/ml and having comparable activity.

(c) A sterile solution according to the procedure of part (a) except that the antibody is the I-131 labeled monoclonal antibody prepared in Example 1, stored in 1% HSA in PBS at a concentration of 20 μg/ml and having comparable activity.

(d) A sterile solution according to the procedure of part (a) except that the antibody is the I-131 labeled antibody against gastrointestinal cancer cell-surface antigens prepared in Example 2(b), stored in 1% HSA in PBS at a concentration of 20 μg/ml and having comparable activity.

(e) A sterile solution according to the procedure of part (a) except that the antibody is the Indium-111 labeled monoclonal antibody against cell-surface antigens of gastrointestinal cancer prepared in Example 2(c), stored in 1% HSA in PBS at a concentration of 20 μg/ml and having comparable activity.

(f) A sterile solution according to the procedure of part (a) except that the antibody is the I-131 labeled monoclonal antibody against breast cancer cell-surface antigens prepared in Example 3, stored in 1% HSA in PBS at a concentration of 20 μg/ml and having comparable activity.

(g) A sterile solution according to the procedure of part (a) except that the antibody is the I-131 labeled monoclonal antibody against cell-surface antigens of human malignant melanoma cells prepared in Example 4, stored in 1% HSA in PBS at a concentration of 20 μg/ml and having comparable activity.

(h) A sterile solution according to the procedure of part (a) except that the antibody is the I-131 labeled boron-containing antibody against breast cancer cell-surface antigens prepared in Example 6, stored in 1% HSA in PBS at a concentration of 20 μg/ml and having comparable activity.

(i) A sterile solution according to the procedure of part (a) except that the antibody is replaced by the technetium-99m-labeled indifferent IgG prepared in Example 5(a), stored in 1% HSA in PBS at a concentration of 20 μg/ml and having comparable activity.

(j) A sterile solution according to the procedure of Example (i) except that the radiolabeled indifferent IgG is the Indium-111-labeled IgG prepared according to Example 5(b), stored in 1% HSA in PBS at a concentration of 20 μg/ml and having comparable activity.

EXAMPLE 10

Colorectal Cancer Imaging

A patient suspected of having a colorectal carcinoma is given a dose of radioiodinated anti-CEA IgG and radiolabeled indifferent IgG according to the procedure of Example 6 of U.S. Ser. No. 126,262. Localization of the tumor for imaging is effected according to the procedure of Goldenberg et al., *N. Engl. J. Med.*, 298, 1384 (1978), by i.v. infusion of equal volumes of solutions of I-131-anti-CEA IgG and Tc-99m-IgG according to Examples 9 (a) or (b) and 9 (i). Myeloma-derived IgG is preferred if repeated imaging studies are required and hypersensitivity to goat immunoglobulin develops. Prior to administration of the reagents i.v., the patient is pretested for hypersensitivity to the antibody preparation (unlabeled) or to IgG of the same species as the antibody preparation. To block thyroid uptake of I-131, Lugol's solution (KI) is administered by mouth, beginning one or more days before injection of the radioiodinated antibody, at a dose of 5 drops twice or three-times daily. Images of various body regions and views are taken at 4, 8, and 24 hours after injection of the labeled preparations. The colorectal carcinoma is demonstrated by gamma camera imaging with subtraction of the Tc-99m counts from those of I-131, as described for I-131-labeled anti-CEA antibody and Tc-99m-labeled human serum albumin by DeLand et al., *Cancer Res.*, 40, 3046 (1980). At 8 hours after injection, imaging is clear, improving with time up to the 24 hr scans. The CEA-selectivity of this method is comparable to the method described in U.S. Ser. No. 126,262, but use of Tc-99m for subtraction is more convenient than I-123, which is less accessible to nuclear medicine laboratories than Tc-99m.

EXAMPLE 11

Gastric Cancer Imaging

A patient with a history of gastric carcinoma and recent signs of possible spread to the liver is evaluated by antibody imaging by a procedure similar to Example 10, using a mixture of solutions of antibodies against CEA and the gastrointestinal cancer surface antigen, labeled with I-131, and MOPC-21 IgG labeled with Tc-99m, according to Examples 9 (b), 9 (d) and 9 (i). Already at 8 hours post i.v. injection, a massive lesion in the right lobe of the liver is revealed by use of gamma camera imaging with subtraction of the Tc-99m counts from those of I-131, as described for I-131-labeled anti-CEA antibody and Tc-99m-labeled human serum albumin by DeLand et al., *Cancer Res.*, 40, 3046 (1980), using procedures described in Example 10. Substitution of the In-111 labeled antibody according to Example 9 (e) for the I-131 labeled antibody mixture, with appropriate subtraction, gives satisfactory localization.

EXAMPLE 12

Breast Cancer Imaging

A woman two-years post-mastectomy for mammary carcinoma is suspected of having a recurrence in the chest. Using the basic approach described in Example 10, solutions of antibody to breast cancer surface antigen labeled with I-131 and the corresponding myeloma IgG (MOPC-21) labeled with Tc-99m, according to Examples 9 (f) and 9 (i), are injected i.v. A mediastinal mass is disclosed by gamma camera imaging, using the subtraction technology described above and the other procedures according to Example 10.

EXAMPLE 13

Radiolabeled Antibody Lymphoscintigraphy

In cancer patients having suspected lymph node spead of their tumors, subdermal or intradermal injection, or even peritumoral injection, of the radiolabeled preparations described in the Examples above can be undertaken. The subtraction procedures described herein are advantageous because they permit specific imaging of cancer-involved lymph nodes at 24 hrs or later following injection, whereas without the subtraction approach, only very immediate lymph nodes draining the tumor site are revealed within a few hours after injection. In a woman with breast cancer having a slightly enlarged ipsilateral axillary node mass, a total of 25–50% of the i.v. radiation dose is administered subcutaneously in the webs of the fingers, as practiced by DeLand et al., *Cancer Res.*, 40, 2997 (1980). Images of the chest obtained at 6, 24, and 48 hours show the best results of axillary lymph node spread at 24 and 48 hours after administration of the reagents according to Examples 9 (f) and 9 (i), with involvement of the mediastinal nodes also seen in the 24 and 48 hr scans. The mediastinal area cannot be revealed by administration of the radiolabeled antibody alone. Reagent compositions with other radiolabels as described above can also be used to reveal breast cancer metastases to lymph nodes by this method of radioantibody lymphoscintigraphy, using the subtraction techniques of the invention.

EXAMPLE 14

Testicular Cancer Imaging

A man with a history of testicular cancer on the right side, removed 2 years earlier, is suspected of having tumor spread to the retroperitoneum. Solutions of the labeled monoclonal antibody preparations according to Example 9 (c), recognizing a germ cell cancer surface antigen, and the corresponding indifferent murine MOPC-21 IgG labeled with In-111 of Example 9 (j) are injected as described in Example 10 for gastrointestinal cancer imaging. Imaging and other procedures are performed as in Example 10, and the retroperitoneal tumors which were missed by ultrasound and transmission computed tomography, are disclosed by gamma camera using and emission. tomography at 24 hours post i.v. injection.

EXAMPLE 15

Therapy of Malignant Melanoma With I-131 Antibodies Against Melanoma Cell Surface Components A patient with disseminated malignant melanoma is given the labeled antibody recognizing cell surface components of malignant melanoma according to Example 9 (g). An intravenous infusion of an I-131 dose of 60 mCi, repeated at two-week intervals for up to a total dose of 180 or 240 mCi (in a 70 kg patient), depending upon whether hematological toxicity occurs at the time of the third dose. The radiolabeled antibody is administered as a slow i.v. infusion in 50 ml of sterile physiological saline. For several days prior to the therapy and during the therapy cycle the patient is given Lugol's solution orally, at 2–3 times 5–10 drops daily, in order to block thyroid uptake of the radioiodinated antibody. A reduction in the size of some of the tumor sites is seen following the third infusion. This therapy cycle is repeated at intervals adjusted on an individual basis, taking into account tumor burden, side effects of the therapy, host toxicity due to other therapy measures, and other factors familiar to the skilled physician.

EXAMPLE 16

Therapy of Testicular Germ Cell Tumor With I-131 Antibodies Against Germ Cell Cancer Surface Components A patient with metastasized embryonal carcinoma of the testis, with tumor in the retroperitoneum and in the left lung, is treated with the I-131-labeled antibody against germ cell cancer surface components according to Example 9 (c). For several days prior to therapy and during the therapy cycle, the patient is given Lugol's solution orally, at 2–3 times 5–10 drops daily, in order to decrease thyroidal uptake of I-131. An I-131 dose of 80 mCi is administered as a slow i.v. infusion in 50 ml of sterile physiological saline, and repeated once monthly for a total of 3 doses. This cycle is then repeated at intervals adjusted on an individual basis. A decrease in the size of the tumor in the left lung is seen after the first therapy cycle. After a second cycle given 3 months later, a decrease in tumor revealed by diagnostic imaging, as in Example 14, is seen in the retroperitoneum.

EXAMPLE 17

Therapy of Disseminated Mammary Cancer With I-131-labeled Antibody Mixtures

A woman whose right breast was removed one year earlier is now admitted for therapy for her recurrences to the chest wall, right axillary nodes, and right lung. After beginning on Lugol's solution, 7 drops 3 times daily, she is given a therapeutic dose of the labeled antibody solution of Example 9 (f), without the Tc-99mlabeled indifferent IgG. A total I-131 dose of 50 mCi is given weekly for a series of 3 weeks, and then repeated at intervals adjusted on an individual basis, e.g., every three months, until hematological toxicity interrupts the therapy. The radioiodinated antibodies are given as a slow i.v. infusion in 50 ml of sterile physiological saline. After the third injection dose, a reduction in the size of the right lung metastasis is noted on a chest roentgenogram, and further reduction of tumor sites is seen after the second therapy cycle, 10 weeks after onset of therapy.

EXAMPLE 18

Therapy of Disseminated Breast Cancer With I-131/B-10 Conjugated Antibodies

A woman with breast cancer disseminated to the chest and lungs is treated with solutions of the antibody preparation labeled with I-131 and with B-10 according to Example 9 (h) and the Tc-99m labeled IgG according to Example 9 (i). She is injected with an amount of I-131 labeled antibody (in 50 ml of sterile physiological saline) sufficient to provide 100 mCi of I-131 activity based on a 70 kg patient weight. This amounts to a dose of antibody IgG of 3.3 mg, having 40–80 Boron atoms and 8–16 Boron-10 atoms per IgG molecule. The tumors are first precisely localized using the procedure of Example 2. The patient is kept on Lugol's solution as in the previous example. A well collimated beam of thermal neutrons is then focused on the defined tumor locations. Irradiation with an external neutron beam dose of 400–800 rads, delivered in a period of from 8–20 min, is effected for each tumor locus, and is optionally repeated with administration of the tumor-locating antibody, with or without the radiolabel, at intervals adjusted on an indidual basis, but usually not exceeding a total dose of 3200 rads unless simultaneous external irradiation therapy is indicated. At least partial remission is observed.

EXAMPLE 19

Therapy of Disseminated Breast Cancer With I-131/B-10-Conjugated Antibody Mixtures A woman with widespread metastases of breast cancer, to the lungs, chest wall, axillary lymph nodes, and vertebral column, is given therapeutic doses of the labeled antibody according to Example 9 (f) and further containing I-131-labeled boron-conjugated anti-CEA antibody according to Example 4 (b) of U.S. Ser. No. 126,262, without the Tc-99m-labeled indifferent IgG, as described in Example 17. The administration of the antibody mixture is effected as in Example 18, but with a radiation dose of 60 mCi I-131 in 2.5 mg IgG protein (half from each of the two kinds of specific antibodies), and with an average boron content of 60 atoms (12 atoms of Boron-10) per IgG molecule. Two to 5 days later, the patient is given a total-body thermal neutron dose, adjusted on an individual basis. The therapy is repeated at intervals adjusted on an individual basis, preferably at 3–5 week intervals, until limiting side effects are observed, to effect at least partial remission.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

I claim:

1. A method for detecting and localizing a tumor having on its cell surface a tumor-associated or tumor-specific antigen, which comprises injecting a human subject parenterally with an antibody specific to said antigen and radiolabeled with a pharmacologically inert radioisotope capable of detection using a photoscanning device, and with indifferent immunoglobulin from the same or different species as that used to prepare said specific antibody, said indifferent immunoglobulin being radiolabeled with a different pharmacologically inert radioisotope emitting at an energy capable of independent detection using said photoscanning device, the radiolabeling being so effected that the kinetics and distribution of the radiolabeled specific antibody and indifferent immunoglobulin in said subject are substantially the same during the time period required for scanning; and scanning the subject with said photoscanning device, the level of activity of the labeled indifferent immunoglobulin being used to determine the distribution of background activity due to non-targeted specific antibody, said background activity being subtracted from the total activity of specific antibody, whereby the activity of substantially only the targeted tumor-localized specific antibody is determined and said tumor is thereby detected and localized.

2. The method of claim 1, wherein said cell surface antigen is carcinoembryonic antigen, a gastrointestinal cancer cell surface antigen, a lung cancer cell surface antigen, a brain tumor cell surface antigen, a glioma cell surface antigen, a breast cancer cell surface antigen, an esophageal cancer cell surface antigen, a common epithelial cancer cell surface antigen, a common sarcoma cell surface antigen, an osteosarcoma cell surface antigen, a fibrosarcoma cell surface antigen, a melanoma cell surface antigen, a gastric cancer cell surface antigen, a pancreatic cancer cell surface antigen, a colorectal cancer cell surface antigen, a urinary bladder cancer cell surface antigen, a prostatic cancer cell surface antigen, a renal cancer cell surface antigen, an ovarian cancer cell surface antigen, a testicular cancer cell surface antigen, an endometrial cancer cell surface antigen, a cervical cancer cell surface antigen, a Hodgkin's disease cell surface antigen, a lymphoma cell surface antigen, a leukemic cell surface antigen or a trophoblastic tumor cell surface antigen.

3. The method of claim 1, wherein the specific antibody is radiolabeled with one of, and the indifferent immunoglobulin is labeled with another of Iodine-131, Iodine-123, Iodine-126, Iodine-133, Bromine-77, Indium-111, Indium-113m, Gallium-67, Gallium-68, Ruthenium-95, Ruthenium-97, Ruthenium-103, Ruthenium-105, Mercury-197, Mercury-203, Rhenium-99m, Rhenium-105, Rhenium-101, Scandium-47, Tellurium-121m, Tellurium-122m, Tellurium-125m, Thulium-165, Thulium-167, Thulium-168, Technetium-99m or Fluorine-18.

4. The method of claim 1, wherein the indifferent immunoglobulin is radiolabeled with a different radioisotope of the same element used to label the specific antibody.

5. The method of claim 1, wherein the specific antibody is a substantially monospecific antibody having a specific immunoreactivity to said antigen prior to labeling of at least 70% and a cross-reactivity to non-tumor-associated antigens of less than 15%.

6. The method of claim 5, wherein said substantially monospecific antibody is a monoclonal antibody.

7. The method of claim 5, wherein said antibody is radiolabeled to an extent sufficient to reduce its specific immunoreactivity to said antigen by about 5-33%.

8. The method of claim 1, wherein the specific antibody is radiolabeled with one of I-131, Tc-99m or In-111 and the indifferent immunoglobulin is radiolabeled with another of I-131, Tc-99m or In-111.

9. The method of claim 1, wherein tumor localization is effected within 48 hours of injection of the labeled immunoglobulins.

10. The method of claim 9, wherein localization is effected within 24 hours of injection.

11. A method of tumor radiotherapy, which comprises parenterally injecting into a human subject having a tumor which produces or is associated with a tumor cell surface antigen a tumor-reducing amount of an antibody which is specific to said antigen and radiolabeled with a pharmacologically inert, radiotherapeutically effective radioisotope; wherein said antibody is substantially monospecific to said antigen, having a specific immunoreactivity prior to labeling of at least 70% and a crossreactivity to other antigens of less than 15%.

12. The method of claim 11, wherein said cell surface antigen is carcinoembryonic antigen, a gastrointestinal cancer cell surface antigen, a lung cancer cell surface antigen, a brain tumor cell surface antigen, a glioma cell surface antigen, a breast cancer cell surface antigen, an esophageal cancer cell surface antigen, a common epithelial cancer cell surface antigen, a common sarcoma cell surface antigen, an osteosarcoma cell surface antigen, a fibrosarcoma cell surface antigen, a melanoma cell surface antigen, a gastric cancer cell surface antigen, a pancreatic cancer cell surface antigen, a colorectal cancer cell surface antigen, a urinary bladder cancer cell surface antigen, a prostatic cancer cell surface antigen, a renal cancer cell surface antigen, an ovarian cancer cell surface antigen, a testicular cancer cell surface antigen, an endometrial cancer cell surface antigen, a cervical cancer cell surface antigen, a Hodgkin's disease cell surface antigen, a lymphoma cell surface antigen, a leukemic cell surface antigen or a trophoblastic tumor cell surface antigen.

13. The method of claim 11, wherein said radioisotope is I-131 or Sc-47.

14. The method of claim 11, wherein the amount of labeled antibody administered in each treatment session carries 25–250 mCi of I-131 radioactivity per 70 kg patient. body weight.

15. The method of claim 11, wherein the radiolabeled antibody is administered in a plurality of divided doses carrying 20–120 mCi of I-131 radioactivity per 70 kg patient body weight per dose.

16. A method of tumor radiotherapy, which comprises the steps of parenterally injecting into a human subject having a tumor which produces or is associated with a tumor cell surface antigen a radiotherapeutically effective amount of an antibody which is specific to said antigen and radiolabeled with a pharmacologically inert radioisotope capable of detection with a photoscanning device, said labeled antibody further comtaining in chemical combination an addend containing at least five atoms of boron with at least a natural abundance of Boron-10 isotope; locating said tumor by scanning the subject with said photoscanning device to determine the location of the resultant uptake of said labeled antibody by said tumor; and directing a beam of thermal neutrons at said tumor location.

17. The method of claim 16, wherein prior to photoscanning, a reference substance is injected into the subject, said reference substance being radiolabeled with a radioisotope emitting at a different energy from the marker-specific antibody label and capable of independent detection by said photoscanning device, the level of activity of said reference substance being used to determine the background activity due to non-targeted specific antibody, said background activity being subtracted from the total activity of the specific antibody, whereby the activity of substantially only the targeted, tumor-associated antibody is determined.

18. The method of claim 17, wherein said reference substance is at least one of technetium-99m-labeled normal human immunoglobulin, technetium-99m-labeled human serum albumin, technetium-99m-sulfur colloid and technetium99m-pertechnetate.

19. The method of claim 17, wherein said reference substance is indifferent immunoglobulin from the same or different species as that used to prepare said specific antibody, said indifferent immunoglobulin being radiolabeled in a manner such that the kinetics and distribution of the radiolabeled specific antibody and indifferent immunoglobulin in said subject are substantially the same during the time period required for scanning.

20. The method of claim 19, wherein said radiolabeled indifferent immunoglobulin is injected concurrently with said radiolabeled marker-specific antibody.

21. A radiolabeled, boron-conjugated antibody which is specific to a tumor-associated or tumor-specific tumor cell surface antigen, said antibody being radiolabeled with a pharmacologically inert radioisotope capable of detection with a photoscanning device, said labeled antibody further containing in chemical combination an addend containing at least five atoms of boron with at least a natural abundance of Boron-10 isotope.

22. The antibody of claim 21, which is specific to carcinoembryonic antigen, a gastrointestinal cancer cell surface antigen, a lung cancer cell surface antigen, a brain tumor cell surface antigen, a glioma cell surface antigen, a breast cancer cell surface antigen, an esophageal cancer cell surface antigen, a common epithelial cancer cell surface antigen, a common sarcoma cell surface antigen, an osteosarcoma cell surface antigen, a fibrosarcoma cell surface antigen, a melanoma cell surface antigen, a gastric cancer cell surface antigen, a pancreatic cancer cell surface antigen, a colorectal cancer cell surface antigen, a urinary bladder cancer cell surface antigen, a prostatic cancer cell surface antigen, a renal cancer cell surface antigen, an ovarian cancer cell surface antigen, a testicular cancer cell surface antigen, an endometrial cancer cell surface antigen, a cervical cancer cell surface antigen, a Hodgkin's disease cell surface antigen, a lymphoma cell surface antigen, a leukemic cell surface antigen or a trophoblastic tumor cell surface antigen.

23. An injectable composition, comprising
(a) an antibody specific to a tumor-associated or tumor-specific tumor cell surface antigen and radiolabeled with a pharmacologically inert radioisotope capable of detection using a photoscanning device;
(b) indifferent immunoglobulin from the same or different species as that used to prepare said specific antibody, said indifferent immunoglobulin being radiolabeled with a different pharmacologically inert radioisotope emitting at an energy capable of independent detection using said photoscanning device; and
(c) a pharmaceutically acceptable injection vehicle;
wherein the radiolabeling is so effected that the kinetics and distribution of the radiolabeled specific antibody and indifferent immunoglobulin will be substantially the same in a human subject during a period of time following injection sufficient for localization and detection.

24. The composition of claim 23, wherein said cell surface antigen is carcinoembryonic antigen, a gastrointestinal cancer cell surface antigen, a lung cancer cell surface antigen, a brain tumor cell surface antigen, a glioma cell surface antigen, a breast cancer cell surface antigen, an esophageal cancer cell surface antigen,, a common epithelial cancer cell surface antigen, a common sarcoma cell surface antigen, an osteosarcoma cell surface antigen, a fibrosarcoma cell surface antigen, a melanoma cell surface antigen, a gastric cancer cell surface antigen, a pancreatic cancer cell surface antigen, a colorectal cancer cell surface antigen, a urinary bladder cancer cell surface antigen, a prostatic cancer cell surface antigen, a renal cancer cell surface antigen, an ovarian cancer cell surface antigen, a testicular cancer cell surface antigen, an endometrial cancer cell surface antigen, a cervical cancer cell surface antigen, a Hodgkin's disease cell surface antigen, a lymphoma cell surface antigen, a leukemic cell surface antigen or a trophoblastic tumor cell surface antigen.

25. The composition of claim 23, wherein the specific antibody is radiolabeled with one of, and the indifferent immunoglobulin is labeled with another of Iodine-131, Iodine-123, Iodine-126, Iodine-133, Bromine-77, Indium-111, Indium-113m, Gallium-67, Gallium-68, Ruthenium-95, Ruthenium-97, Ruthenium-103, Ruthenium-105, Mercury-197, Mercury-203, Rhenium-99m, Rhenium-105, Rhenium-101, Scandium-47, Tellurium-121m, Tellurium-122m, Tellurium-125m, Thulium-165, Thulium-167, Thulium-168, Technetium-99m or Fluorine-18.

26. The composition of claim 23, wherein the indifferent immunoglobulin is radiolabeled with a different radioisotope of the same element used to label the specific antibody.

27. The composition of claim 23, wherein the specific antibody is labeled with one of I-131, Tc-99m or In-111 and the indifferent immunoglobulin is labeled with another of I-131, Tc-99m or In-111.

28. The composition of claim 23, wherein the specific antibody is a monoclonal antibody and the indifferent immunoglobulin is myeloma protein.

* * * * *

UNITED STATES PATENT AND TRADEMARK OFFICE
CERTIFICATE OF CORRECTION

PATENT NO.    :  4,444,744
DATED         :  April 24, 1984
INVENTOR(S)   :  Milton D. Goldenberg It is certified that error appears in the above-identified patent and that said Letters Patent is hereby corrected as shown below:

Title page, field 63: reads "Continuation-in-part of Ser. No. 126,262,
Mar. 3, 1980, abandoned."
should read -- Continuation-in-part of Ser. No.
126,262, Mar. 3, 1980, now U.S. Patent 4,348,376,
September 7, 1982. --

Column 1,, line 11: reads "now abandoned, the disclosure of which is
incorporated"
should read -- now U.S. Patent 4,348,376, Sept. 7, 1982,
the disclosure of which is incorporated -- .

Signed and Sealed this

Sixth Day of November 1984

[SEAL]

Attest:

GERALD J. MOSSINGHOFF

*Attesting Officer*    *Commissioner of Patents and Trademarks*